United States Patent
Buckley et al.

(10) Patent No.: US 6,841,095 B2
(45) Date of Patent: Jan. 11, 2005

(54) CHEMICAL PROCESS AND PLANT

(75) Inventors: Glyn Jeffrey Buckley, Wigan (GB);
Michael Joseph Bowe, Preston (GB);
John William Stairmand, Chester (GB)

(73) Assignee: Accentus PLC, Didcot (GB)

(*) Notice: Subject to any disclaimer, the term of this patent is extended or adjusted under 35 U.S.C. 154(b) by 37 days.

(21) Appl. No.: 10/343,786

(22) PCT Filed: Sep. 5, 2001

(86) PCT No.: PCT/GB01/03982
§ 371 (c)(1),
(2), (4) Date: Feb. 4, 2003

(87) PCT Pub. No.: WO02/20151
PCT Pub. Date: Mar. 14, 2002

(65) Prior Publication Data
US 2003/0168330 A1 Sep. 11, 2003

(30) Foreign Application Priority Data
Sep. 8, 2000 (GB) .............................................. 0022016

(51) Int. Cl.⁷ ................................................. C07F 1/02
(52) U.S. Cl. ................................................... 260/665 R
(58) Field of Search ...................................... 260/665 R

(56) References Cited
FOREIGN PATENT DOCUMENTS
WO    00/35579    *   6/2000

* cited by examiner

Primary Examiner—J. Parsa
(74) Attorney, Agent, or Firm—William H. Holt

(57) ABSTRACT

A chemical plant for performing a chemical reaction between particles of a material such as lithium metal, and a reagent such as butyl chloride in solution in hexane, in which one reaction product is a solid material, includes a reaction vessel (12). Several ultrasonic transducers (16) are attached to a wall of the vessel (12) so as to irradiate ultrasonic waves into the vessel, the vessel being large enough that each transducer irradiates into fluid at least 0.1 m thick, each transducer irradiating no more than 3 W/cm2, and the transducers being sufficiently close to each other and the number of transducers being sufficiently high that the power dissipation within the vessel is at least 10 W/liter but no more than 200 W/liter. The high intensity of ultrasound ensures that lithium chloride is cleaned off the surface of lithium metal particles throughout the vessel (12).

7 Claims, 1 Drawing Sheet

CHEMICAL PROCESS AND PLANT

This invention relates to a method and an apparatus for carrying out chemical reactions that involve a reaction between a material in particulate form and a liquid, in which a product of the reaction is a solid which tends to form a coating on the particulate material.

The invention is particularly suitable for reactions involving alkaline metals, as these metals are highly reactive but are soft and so not easy to pump. Chemical reactions with such metals may be performed with the metal in the form of particles in suspension in an inert liquid, the liquid acting as a solvent for a material with which the metal reacts. For example, lithium metal may be reacted with butyl chloride in solution in a solvent such as hexane. Formation of a layer of salt on the surface of the metal particles can suppress this reaction. It is also desirable to ensure that the metal is always exposed, otherwise side reactions may instead occur, for example butyl chloride may react with the desired product, butyl lithium.

According to the present invention there is provided a method of performing a chemical reaction between a first material and a reagent, the reaction being carried out between the first material in particulate form and a liquid that comprises the reagent, one reaction product being a solid material, the method comprising contacting the first material and the reagent in a plant, the plant comprising at least one reaction vessel with a plurality of ultrasonic transducers attached to a wall of the vessel so as to irradiate ultrasonic waves into the vessel, the vessel being large enough that each transducer irradiates into fluid at least 0.1 m thick, each transducer irradiating no more than 3 W/cm$^2$, and the transducers being sufficiently close to each other and the number of transducers being sufficiently high that the power dissipation within the vessel is at least 10 W/liter but no more than 200 W/liter, stirring the contents of the reaction vessel, and energising the transducers.

The values of power given here are those of the electrical power delivered to the transducer or the transducers, as this is relatively easy to determine. There will inevitably be losses in converting electrical to acoustic power, and in transmitting the acoustic power from the transducer into the fluid within the vessel, but these are difficult to assess accurately. The transducer is typically at least 90% efficient in converting electrical to acoustic power.

The power radiated by each transducer may for example be in the range 1–2 W/cm$^2$. This is a similar ultrasonic power intensity to that used in ultrasonic cleaning baths, and is above the threshold required to achieve cavitation. Although it is possible to achieve higher powers, such as 10 W/cm$^2$, the lower intensity ultrasound specified in the present invention can propagate much further through a liquid, and the stresses in the transducers are reduced.

All the transducers may be energized simultaneously, or alternatively groups of transducers may be energized sequentially. The transducers may all be energized at the same frequency, for example 20 kHz, or alternatively groups of transducers may be energized at different frequencies for example 20 kHz and 40 kHz. The actual frequency or frequencies of operation are not usually critical, but might be as high as 140 kHz or even 200 kHz, as such high frequencies tend to reduce the risk of cavitation erosion.

For the reaction between lithium metal and butyl chloride the particles of lithium metal are preferably larger than 1 mm in size, for example between 3 mm and 10 mm, or about 5 mm. Particles of lithium chloride are formed by the chemical reaction, and are dislodged from the surface of the lithium particles by the ultrasonic irradiation; these particles are typically smaller than 0.1 mm in size. Preferably the vessel has an outlet port through which liquid from the vessel can be extracted, and preferably this outlet port is provided with a coarse mesh or strainer so that the lithium particles are kept in the vessel.

BRIEF DESCRIPTION OF THE DRAWING

The invention will now be further and more particularly described, by way of example only, and with reference to the accompanying drawing which shows a chemical plant for making n-butyl lithium.

DETAILED DESCRIPTION OF THE INVENTION

Figure 1:
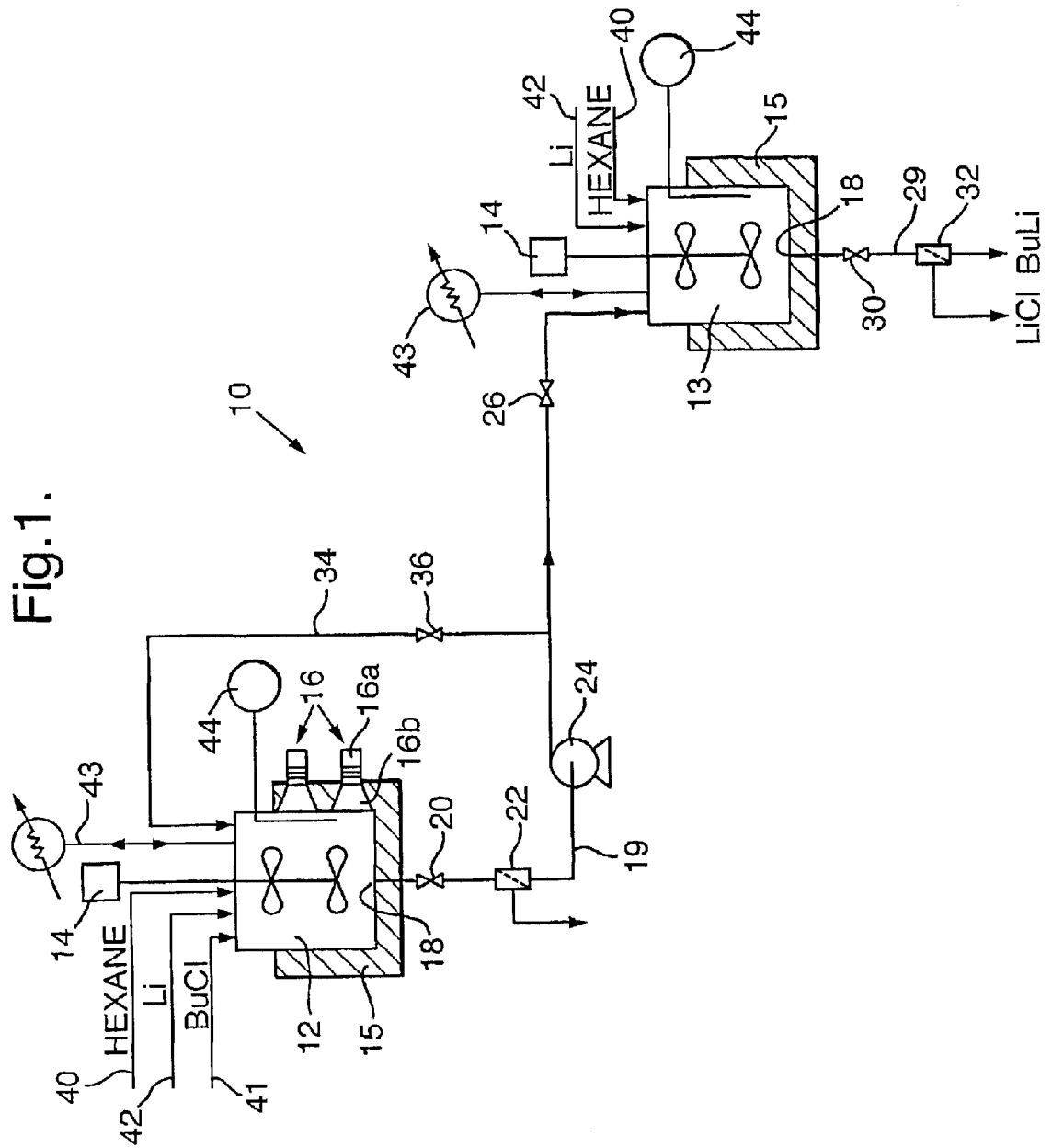

N-butyl lithium is made by reacting butyl chloride with lithium metal, in for example hexane as a solvent for the butyl chloride and in which the lithium metal can be suspended. This reaction may be carried out using very fine lithium metal particles, but the production and use of such fine metal particles is potentially hazardous. Use of large pieces of lithium metal has not been found practical, because lithium chloride forms a surface layer that suppresses further reaction.

The chemical plant 10 comprises two substantially identical reaction vessels 12, 13, each provided with a variable speed multi-stage agitator 14. Each is also provided with a temperature control jacket 15. Each is of stainless-steel, of wall thickness 2 mm, and to the outside of the wall are attached a large number of transducer modules 16 (for example between fifty and a hundred; two are shown, not to scale). Each such transducer module 16 consists of a 50 W piezoelectric transducer 16a which resonates at 20 kHz, attached to a conically flared titanium coupling block 16b by which it is connected to the outside of the wall, the wide end of each block 16b (where it is connected to the wall) being of diameter for example 63 mm, so that each transducer module 16 irradiates 50 W over a circle of diameter 63 mm, that is an intensity of 1.6 W/cm$^2$. The modules 16 form an array covering substantially the entire wall of each vessel 12 or 13. The energy from all the transducers 16a is dissipated over the entire volume of the vessel 12 or 13, and the number of transducer modules 16 is such that the power density is preferably about 50 or 60 W/liter.

All the transducers 16a may, as described, resonate at 20 kHz, but alternatively some of them may instead resonate at a different frequency such as 40 kHz. All the transducers 16a may be energized simultaneously, or alternatively groups of adjacent transducers 16a may be energized sequentially. For example all the transducers, 16a on one side of the vessel may be energized as a common group, and then all the transducers 16a on the opposite side.

Each vessel 12, 13 is also provided with an outlet port 18 covered by a coarse mesh so that only particles less than 2 mm across can pass through. An outlet duct 19, in which is a valve 20, an inline filter unit 22, a pump 24, and a cut-off valve 26, connects the outlet port 18 of the first vessel 12 to an inlet of the second vessel 13. The outlet port 18 of the second vessel 13 is similarly provided with an outlet duct 29 in which is a valve 30, and an inline filter unit 32. Downstream of the pump 24 a recirculation duct 34-with a cut-off valve 36 connects the duct 19 to a recirculation inlet of the vessel 12.

The first vessel 12 is provided with inlets 40, 41 and 42 for hexane, butyl chloride, and-particles of lithium metal respectively, and a reflux condenser 43. It is also provided with a thermometer 44. The second vessel 13 is similarly provided with inlets 40 and 42, for hexane and lithium metal respectively, a reflux condenser 43, and a thermometer 44. In each case the lithium metal is provided in pieces about say 5 mm across; their exact shape and size are not critical, and the lithium may be in large-blocks, for example 0.1 m cubes, or rods say 10 mm diameter and 0.1 m long, or cylindrical pieces say 20 mm long cut from a bar of diameter 5 mm or 10 mm. Means are also provided (not shown) for purging the vessels 12 and 13 with argon.

In use of the plant 10, the first vessel 12 after being purged with argon is charged with hexane and lithium metal particles through the inlets 40 and 42, and the agitator 14 is activated to thoroughly mix and circulate the contents of the vessel 12. The vessel 12 is initially heated, using the jacket 15, to a temperature of 50° C. Butyl chloride is then gradually added through the inlet 41. The butyl chloride reacts exothermically with the lithium metal forming the desired product, butyl lithium, and also forming lithium chloride. The temperature of the vessel 12 is controlled by controlling the rate at which the butyl chloride is added, and if necessary by supplying a coolant to the jacket 15. The temperature of the hexane may rise to its boiling point of 69° C., but any hexane which evaporates is returned to the vessel 12 by the condenser 43. The ultrasonic transducer modules 16 on the wall of the vessel 12 are energized so that the contents are subjected to high intensity ultrasound for example at 60 W/liter, which breaks off small particles of lithium chloride from the surface of the lithium metal particles.

By opening the valves 20 and 36 (and closing the valve 26) and energising the pump 24, liquid from the vessel 12 may be recirculated through the filter 22. Lithium metal particles are too large to pass through the mesh at the outlet port 18; and so remain in the vessel 12. The filter 22 consequently removes lithium chloride, which is in the form of particles typically of size in the range 1 $\mu$m–100 $\mu$m. By opening the valves 20 and 26 (and closing the valve 36) and energising the pump 24, liquid from the vessel 12 may instead be passed into the second vessel 13. This would be done after first purging the second vessel 13 with argon and charging it with hexane and lithium metal. Consequently any unreacted butyl chloride carried into the second vessel 13 is exposed to a large excess of lithium metal, with which it reacts. This suppresses the risk of side reactions. The second vessel 13 is also subjected to high intensity ultrasound in the same way as is the first vessel 12.

Finally the solution of butyl lithium in hexane can be discharged through the outlet duct 29 of the second vessel 13, through the filter 32 which removes the particles of lithium chloride, the much larger pieces of lithium metal being trapped by the coarse mesh at the outlet port 18.

It will be appreciated that a chemical reaction plant may differ from that described above while remaining within the scope of the present invention, and that some details will depend upon the chemical reagents involved. For example in the above reaction an alternative solvent may be used, such as cyclohexane which boils at 81° C. The plant may also differ, for example the vessels 12 and 13 might instead be made of a different material such as polytetrafluoroethylene, and the ultrasonic transducer modules 16 might be coupled indirectly to the vessel, being attached to a slightly larger, concentric wall, the space between the inner and outer walls being filled with a coupling liquid such as olive oil that has a higher threshold for cavitation than the solvent such as hexane used in the vessels. The gap between the concentric walls is preferably a quarter of the wavelength of the ultrasound; the oil in the gap helps match the impedance between the titanium coupling block and the solution in hexane, so that more of the applied power enters the reacting fluids within the vessel.

What is claimed is:

1. A method of performing a chemical reaction between a first material and a reagent, the reaction being carried out between the first material in particulate form and a liquid that comprises the reagent, one reaction product being a solid material that tends to form a coating that suppresses the reaction, the method comprising contacting the first material and the reagent in a plant, the plant comprising at least one reaction vessel with a plurality of ultrasonic transducers attached to a wall of the vessel so as to irradiate ultrasonic waves into the vessel, the vessel being large enough that each transducer irradiates into fluid at least 0.1 m thick, each transducer irradiating no more than 3 W/cm$^2$, and the transducers being sufficiently close to each other and the number of transducers being sufficiently high that the power dissipation within the vessel is at least 10 W/liter but no more than 200 W/liter, stirring the contents of the reaction vessel, and energizing the transducers.

2. A method as claimed in claim 1 in which the power radiated by each transducer is in the range 1–2 W/cm$^2$.

3. A method as claimed in claim 1 wherein the transducers are energized simultaneously.

4. A method as claimed in claim 1 wherein groups of transducers are energized sequentially.

5. A method as claimed in claim 1 wherein each vessel has an outlet port through which liquid from the vessel can be extracted, and this outlet port is provided with a coarse mesh or strainer so that the particles of the first material are kept in the vessel.

6. A method of carrying out a chemical reaction between lithium metal and butyl chloride, the reaction being carried out between particles of lithium metal and a liquid that comprises butyl chloride, wherein the particles of lithium metal are larger than 1 mm in size, the method comprising contacting the lithium particles and the butyl chloride in a plant, the plant comprising at least one reaction vessel with a plurality of ultrasonic transducers attached to a wall of the vessel so as to irradiate ultrasonic waves into the vessel, the vessel being large enough that each transducer irradiates into fluid at least 0.1 m thick, each transducer irradiating no more than 3 W/cm$^2$, and the transducers being sufficiently close to each other and the number of transducers being sufficiently high that the power dissipation within the vessel is at least 10 W/liter but no more than 200 W/liter, stirring the contents off the reaction vessel, and energizing the transducers.

7. A method as claimed in claim 6 wherein the particles of lithium metal are of size between 3 mm and 20 mm.